(12) United States Patent
Nissilä et al.

(10) Patent No.: US 6,616,612 B1
(45) Date of Patent: Sep. 9, 2003

(54) MEASURING ARRANGEMENT (75) Inventors: Seppo Nissilä, Oulu (FI); Jari Miettinen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/522,576

(22) Filed: Mar. 10, 2000

(30) Foreign Application Priority Data

Mar. 12, 1999 (FI) .................................................. 990553

(51) Int. Cl.$^7$ ................................................. A61B 5/00
(52) U.S. Cl. ........................ 600/485; 600/500; 600/503
(58) Field of Search ............................... 600/481, 485, 600/500–504, 508–509

(56) References Cited

U.S. PATENT DOCUMENTS

| | | | |
|---|---|---|---|
| 4,252,128 A | | 2/1981 | Kane |
| RE33,518 E | * | 1/1991 | McCord et al. |
| 5,186,054 A | * | 2/1993 | Sekimura ..................... 73/724 |
| 6,132,382 A | * | 10/2000 | Archibald et al. ...... 600/500 X |
| 6,151,968 A | * | 11/2000 | Chou ........................... 73/748 |
| 6,210,340 B1 | * | 4/2001 | Amano et al. ............... 600/500 |
| 6,331,161 B1 | * | 12/2001 | Chesney ..................... 600/500 |

FOREIGN PATENT DOCUMENTS

| | | | |
|---|---|---|---|
| EP | 0 452 578 A1 | 10/1991 | |
| FI | 932881 | 12/1994 | |
| WO | WO 95/00070 | 5/1995 | |
| WO | 9842254 | * 10/1998 | ................. 600/500 |

* cited by examiner

*Primary Examiner*—Robert L. Nasser
(74) *Attorney, Agent, or Firm*—Hoffmann & Baron, LLP (57) ABSTRACT

The invention relates to a measuring arrangement for measuring a pressure signal from a living body. The measuring arrangement comprises a sensor structure comprising a converter for converting the effect of the pressure signal measured from the body into an electrical signal. The measuring arrangement of the invention comprises a pressure transmission structure prior to the converter in the sensor structure, the pressure transmission structure comprising one or more pressure transmission elements. The pressure transmission structure is, through one or more pressure transmission elements, meant to be in direct or indirect contact with the body for detecting the pressure signal measurable from the body. The pressure transmission structure is, through one or more pressure transmission elements, connected to the converter for transmitting the effect of the pressure signal detected in the body to the converter in the sensor structure by means of one or more pressure transmission elements of the pressure transmission structure.

28 Claims, 8 Drawing Sheets

MEASURING ARRANGEMENT

BACKGROUND OF THE INVENTION

Field of the Invention

The invention relates to a measuring arrangement for measuring a pressure signal from a living body, which measuring arrangement comprises a sensor structure comprising a converter for converting the effect of the pressure signal measured from the body to an electrical signal.

The invention is applied in particular to wristband-type heart rate monitors which by means of the measuring arrangement measure the pressure pulse signal of the wrist artery and, on the basis thereof, determine the heart rate. Another field of application is the pressure pulse measurement required in blood pressure measurement. The invention is especially well suited for multi-channel measurement, in which the sensor structure of the measuring arrangement comprises several measuring channels.

In known measuring arrangements the sensor, i.e. in practice, the converter in the sensor, is flat and in direct contact with skin. The measuring point, such as the area of the wrist artery, is, however, an area which does not allow a flat sensor to settle well enough against the skin. This problem is accentuated in multi-channel sensors in which the sensor is considerably wider than in one-channel sensors. A flat sensor also provides the disadvantage that, by means of it, it is not possible to mechanically amplify the signal that is transmitted from the artery to the signal converter. Thus, the drawback in known measuring arrangements is too poor a measuring sensitivity.

SUMMARY OF THE INVENTION

It is thus an object of the invention to develop a novel measuring arrangement so as to reduce the problems and drawbacks related to the known solutions.

To achieve the above-mentioned objective, the measuring arrangement of the invention is characterized in that it comprises a pressure transmission structure prior to the converter in the sensor structure, the pressure transmission structure comprising one or more pressure transmission elements, and which pressure transmission structure is, through one or more pressure transmission elements, meant to be in direct or indirect contact with the body for detecting the pressure signal measurable from the body, and which pressure transmission structure is, through one or more pressure transmission elements, connected to the converter for transmitting the effect of the pressure signal detected in the body to the converter in the sensor structure by means of one or more pressure transmission element.

The idea of the invention is based on a pressure transmission structure implemented by means of one or more pressure transmission elements, and its suitable design.

The method and arrangement of the invention provide the advantage that the sensor settles better than before against the measuring point, for instance against the wrist at the wrist artery. The invention also in a way raises what is known as the sensitive surface of the sensor to a sufficient distance from the converter in the measuring arrangement and the other structures whose operation involves electrical signals. The sensitive surface of the sensor, i.e. the pressure transmission elements, is on the surface of the measuring arrangement, but the structures whose operation involves electrical signals can be kept deeper in the apparatus and thus at a distance from the skin and better protected against the loads from the operating environment. In addition, a preferred embodiment of the invention provides mechanical amplification for the effect of a pressure signal, which effect is transmitted from the first edge of the pressure transmission element through the second edge of the element to the signal converter. The preferred embodiments of the invention emphasize the advantages provided by the basic invention.

BRIEF DESCRIPTION OF THE DRAWINGS

In the following, the invention will be described by means of preferred embodiments and with reference to the attached drawings, in which.

DETAILED DESCRIPTION OF THE INVENTION

Figure 4:
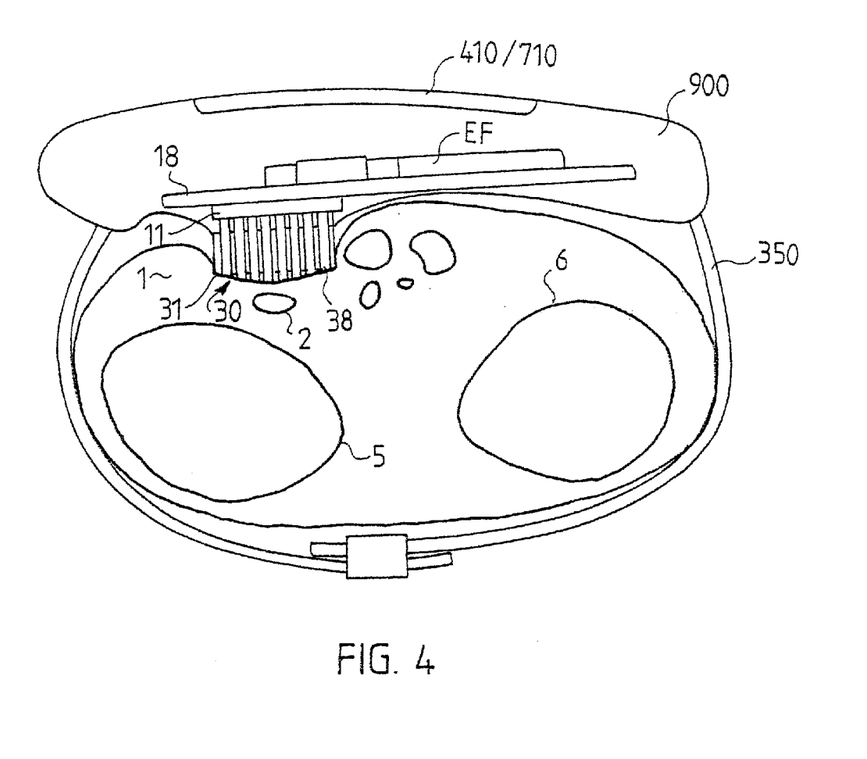
FIG. 4 shows a measuring arrangement integrated to a wristband.
Figure 9:
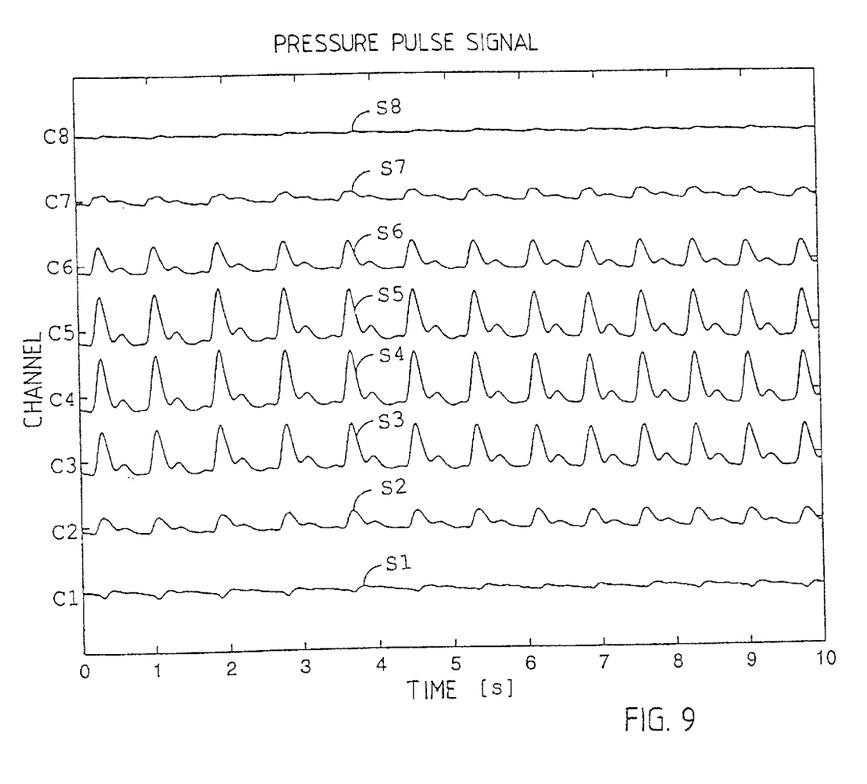
FIG. 9 shows the pressure pulse signals of eight channels.

The invention relates to a measuring arrangement for measuring a pressure signal from a living body 1. In the figures, the body is represented by a hand 1 having an artery 2, such as a wrist artery 2. In FIG. 4, the reference numbers 5 and 6 represent the radius and the ulna. Most preferably, the measuring arrangement is used to measure the pressure pulse signal from the wrist artery 2. FIG. 9 shows a pressure pulse signal which, in fact, is the pressure pulse signals S1 to S8 of eight measuring channels C1 to C8.

The measuring arrangement comprises a sensor structure 10 which comprises a converter 11 for converting the effect of the pressure signal measured from the body 1 to an electrical signal. The converter 11 is most preferably a capacitive converter 11, as in FIG. 1, or in a second preferred embodiment, a resistive converter 111, as in FIG. 8.

Figure 2:
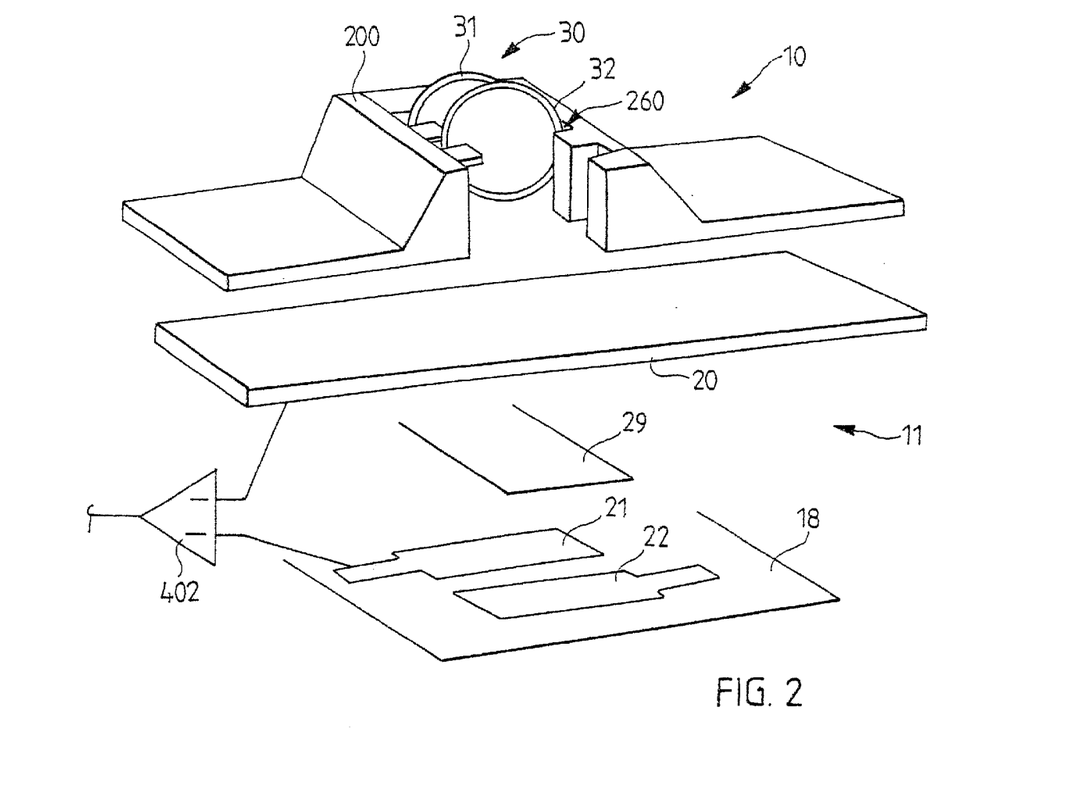
FIG. 2 is a chart showing the principle of a two-channel measuring arrangement having a capacitive converter, with the structural parts being separated from each other for the purpose of illustration.
Figure 3:
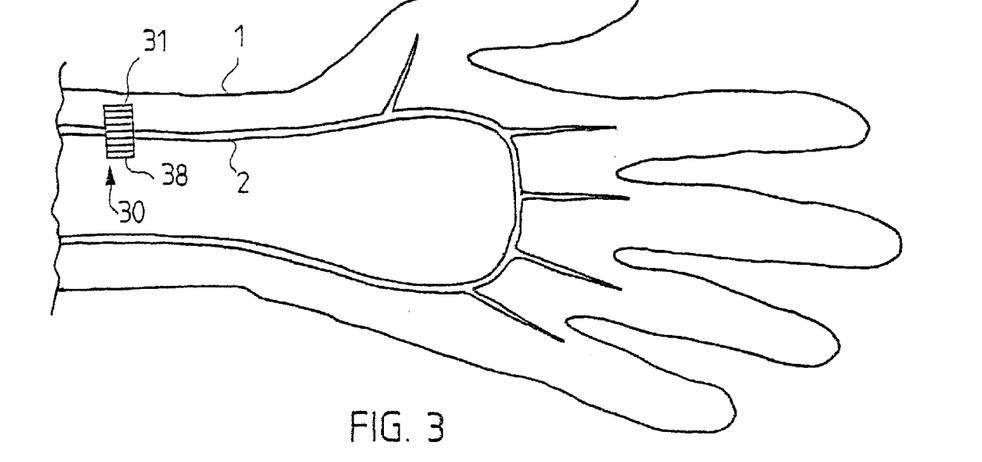
FIG. 3 is a chart showing the principle of placing a pressure transmission element in relation to the wrist artery.

The figures show that the measuring arrangement comprises a pressure transmission structure 30 prior to the converter 11 in the sensor structure 10, the pressure transmission structure comprising one or more pressure transmission elements 31 to 38. In the example of FIG. 2, there are two pressure transmission elements. In the examples of FIGS. 3 to 6, there are eight pressure transmission elements. The pressure transmission structure 30 is in a way a connecting piece between the sensitive area of the measuring arrangement, i.e. the converter 11, and the measurement target 1, i.e. the body 1.

The figures show that the pressure transmission structure 30 is, through one or more pressure transmission elements 31 to 38, meant to be in direct or indirect contact with the body 1 for detecting the pressure signal S1 to S8 measurable from the body 1, for instance from an artery 2. In addition, the pressure transmission structure 30 is, through one or more pressure transmission elements 31 to 38, connected to the converter 11 for transmitting the effect of the pressure signal detected in the body 1 to the converter 11 in the sensor structure 10 by means of one or more pressure transmission elements 31 to 38 of the pressure transmission structure 30. With reference to the above-mentioned indirect contact, it should be noted that as in FIG. 1, a dust shield 15 or another structure making the contact indirect can be arranged between the skin and the pressure transmission structure 30.

Even though several pressure transmission elements, for instance all 8 pressure transmission elements 31 to 38, can be and, in practice, are simultaneously in contact with the body 1 for detecting the pressure pulse of the artery 2, it is naturally understandable that all pressure transmission elements 31 to 38 do not necessarily detect a pressure pulse and thus, cannot transmit an effect to the converter 11. Such a situation may arise, if in the vicinity of some pressure transmission elements in the body 1, there is no pressure pulse signal strong enough to transmit to a pressure transmission element. For instance, it may be that three or four pressure transmission elements move towards the converter 11 and the remaining five or four elements do not move, because the pressure signal at their location in the body is too weak to create the movement of the pressure transmission elements in question towards the converter 11. In the channels C3 to C5 of FIG. 9, the signals S3 to S5 are quite strong and thus affect the pressure transmission elements 33 to 35 detecting the signals S3 to S5.

Figure 5:
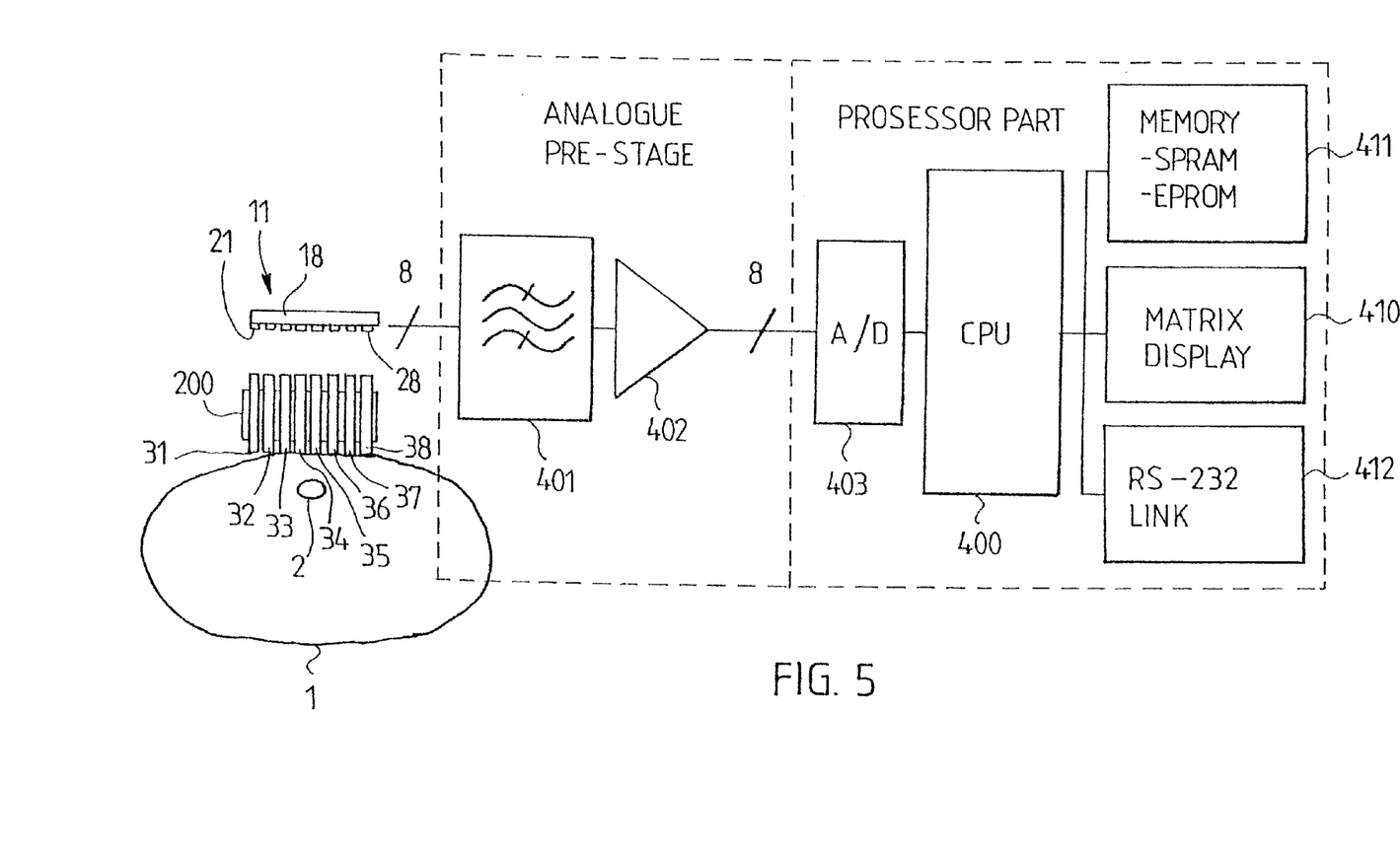
FIG. 5 is a chart showing the principle of a measuring arrangement as applied to heart rate measurement.
Figure 6:
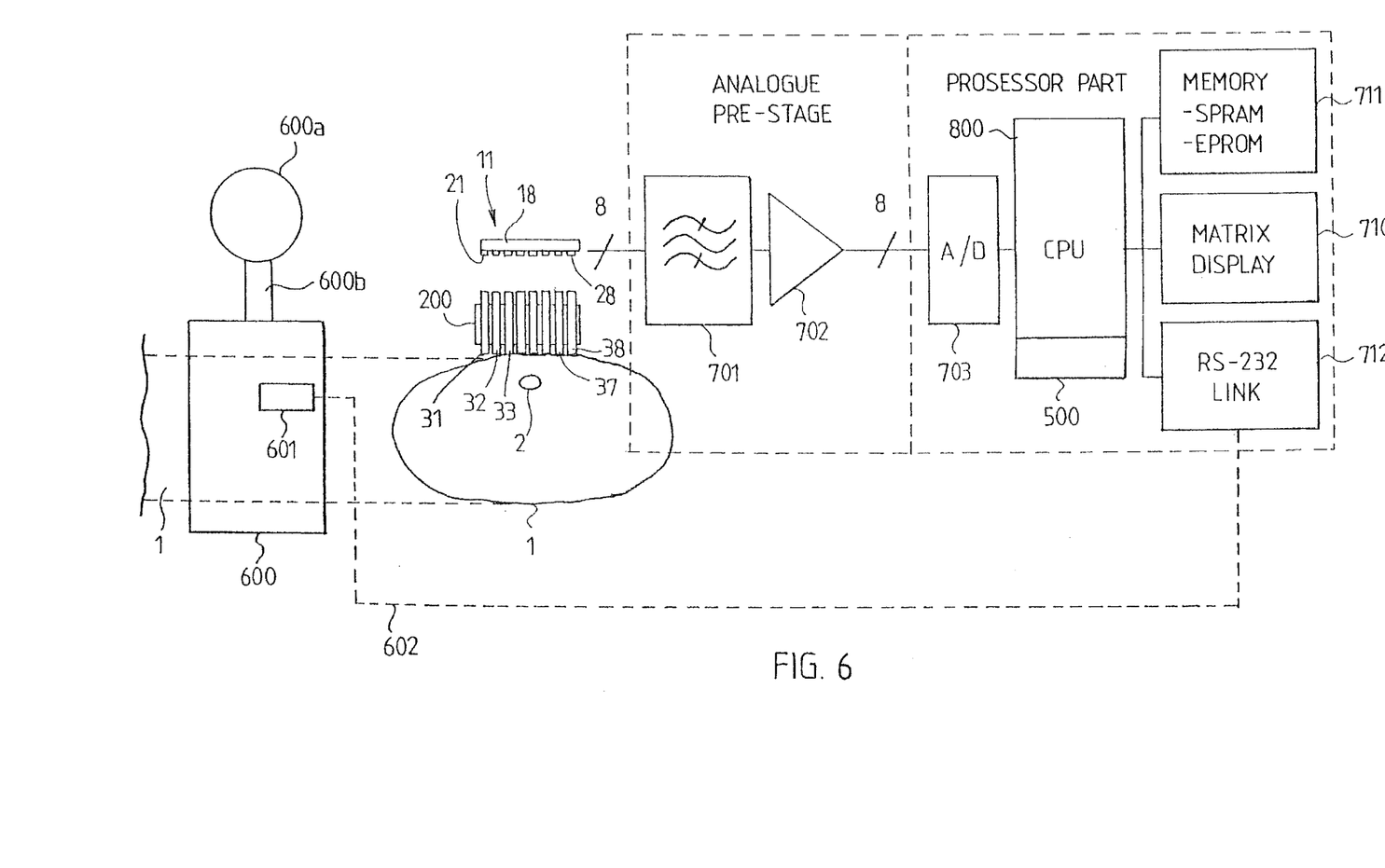
FIG. 6 is a chart showing the principle of a measuring arrangement for measuring a pressure pulse in blood pressure measurement.

In the preferred embodiment of FIGS. 1 to 2 and 5 to 6, the converter 11 in the sensor structure, to which the pressure transmission structure 30 is connected, is a capacitive converter 11 whose capacitance changes according to the pressure transmitted by the pressure transmission structure 30 to the converter. A capacitive converter 11 is most preferably implemented in such a manner that the capacitive converter 11 comprises a conductive ground plane 20, one or more conductive signal outputs 21 to 28, and an intermediate part 29 between the ground plane 20 and the signal outputs 21 and 28. The structure is thus similar in principle to that of a capacitor, i.e. an intermediate part 29, which is most preferably made of a dielectric material, is located between the conductive surfaces, i.e. the ground plane 20 and the signal outputs 21 and 28. The intermediate part 29 should in this application be collapsible to allow the movement of the pressure transmission elements 31 to 38 towards the signal outputs. For instance, when the pressure transmission element 31 moves towards the converter 11, the distance between the ground plane 20 and the signal output 21 becomes shorter, changing the capacitance of the converter 11. The capacitance change in question alters the current running in the circuit passing through the ground plane 20 and the signal output 21, and the alteration of the current is detected in the apparatus, for instance in blocks 400 (FIG. 5) or blocks 500 and 800 (FIG. 6). The operation is similar in the rest of the pressure transmission elements 32 to 38 and the corresponding signal outputs 22 to 28. The signal outputs 21 to 28 are conductive areas formed on the surface of a platform 18, such as a circuit board 18 or another suitable platform 18, as shown in FIGS. 1 to 2 and 5 to 6.

A preferred embodiment shows that the pressure transmission structure 30, 31 to 38 is connected to the converter through the ground plane 20 of the converter 11.

The converter 11, for instance a capacitive converter 11, can be a PVDF-type (polyvinyl difluoride) converter based on a piezoelectric effect, or the converter 11 can be an EMF (electromechanical film) converter based on an electret film, because these do not require a power supply, since piezo or EMF elements have an electric charge of their own. The intermediate part 29 of a capacitive converter 11 can thus most preferably be piezoelectric or electret (EMF).

Figure 8:
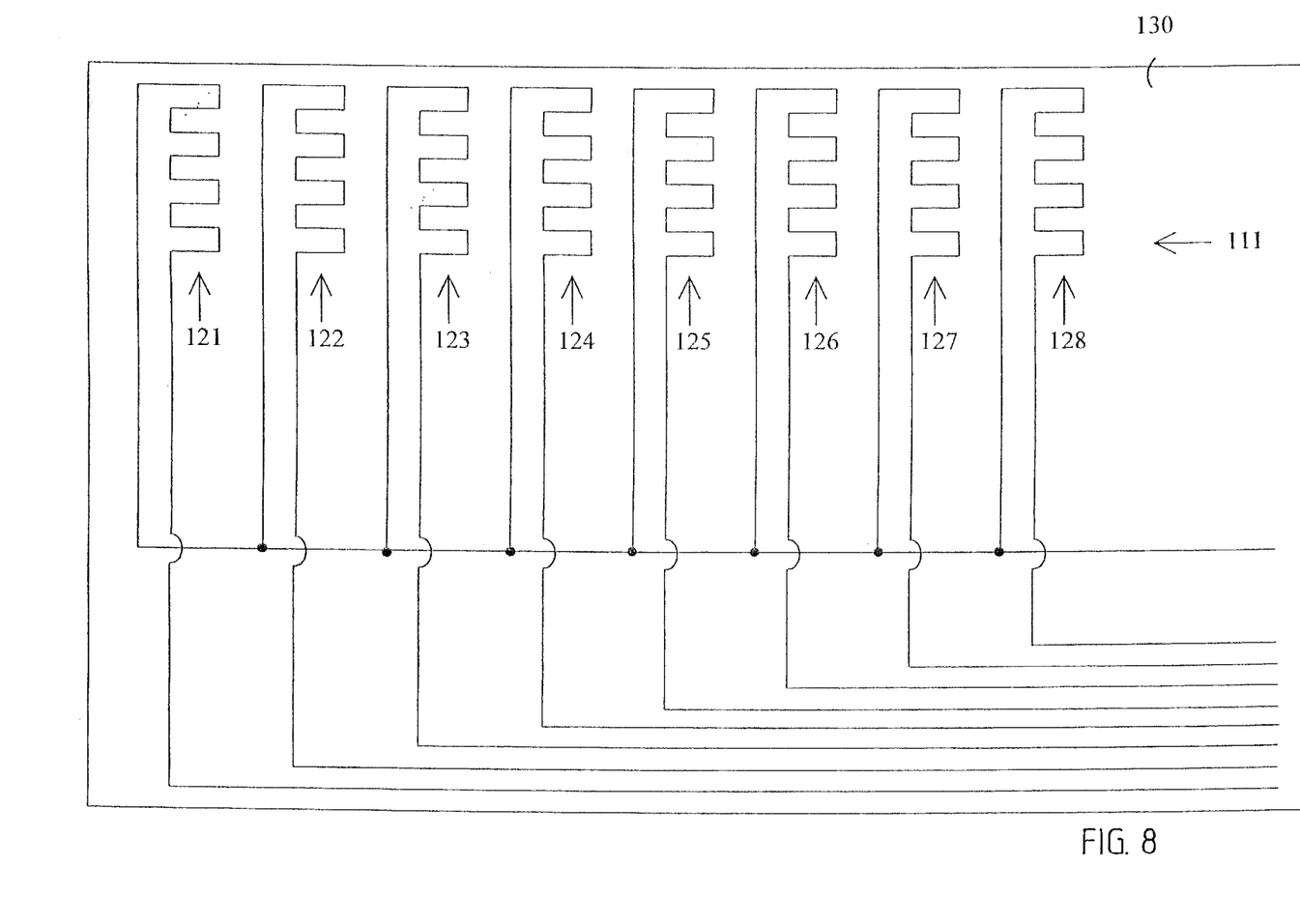
FIG. 8 shows a resistive converter as seen from the direction of the pressure transmission structure.

The converter 11 presented above is thus capacitive. Alternatively, the measuring arrangement can be as in FIG. 8, i.e. the converter 111 comprising a sensor structure, to which the pressure transmission structure 30 is connected, is a resistive converter 111 whose resistance changes according to the pressure transmitted by the pressure transmission structure 30, 31 to 38 to the converter. The operation of the resistive converter is based on the fact that the pressure transmission elements 31 to 38 press the flexible resistive converter 111 making it bend and consequently, due to the bending, its resistance changes. The change in the resistance alters the electrical signal received from the converter 111. In FIG. 8, the resistive converter 111 comprises resistive elements 121 to 128 whose number corresponds to that of the pressure transmission elements 31 to 38, i.e. the pressure pulse transmission elements 31 to 38, and which are paired with the pressure transmission elements 31 to 38, i.e. the pressure transmission element 31, for instance, is arranged to press the resistive element 121, and the resistive element 121 bends making its resistance change and thus causing an alteration in the current, which is then detected. The alteration of the current indicates, whether there was a pressure pulse and how strong it was. The resistive elements 121 to 128 are signal outputs like the signal outputs 21 to 28 of the capacitive sensor. The pressure transmission elements 31 to 38 settle against the pointed areas of the resistive elements 121 to 128, i.e. the movement of the pressure transmission elements 31 to 38 is directed at the pointed areas. In FIG. 8, the free ends of the horizontal lines of the resistive elements 121 to 128 are, in practice, connected to a filter 401 or 701 as shown in FIG. 5 or 6. The signal outputs 121 to 128 are made of a resistive coating or a resistive conductor on the surface of the platform 130, for instance a circuit board or the like.

Figure 1:
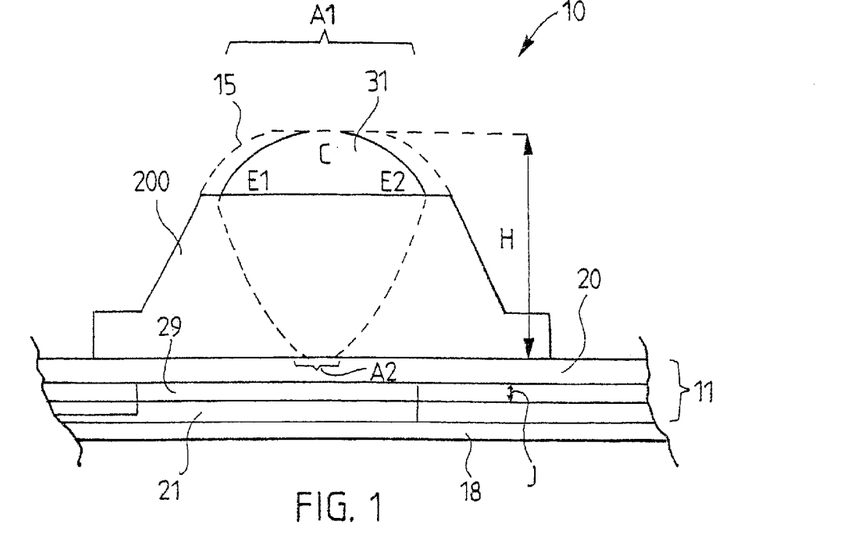
FIG. 1 shows a one-channel measuring arrangement having a capacitive converter.

By suitably designing the pressure transmission elements 31 to 38, an even better operation is achieved in a preferred embodiment of the invention. Let us mark as A1 the surface area of the area which is to be against the body 1 in the pressure transmission element 31 and as A2 the surface area of the area which is against the converter 11 in the same pressure transmission element 31. According to a preferred embodiment, the figures, for instance FIG. 1, show, for the pressure transmission element 31, for instance, that in a preferred embodiment, in one or more pressure transmission elements 31 to 38, the surface area A1, which is to be against the body 1 and which is meant to detect the pressure signal of the body 1, is greater than the surface area A2, which is against the converter 11 in the same pressure transmission element 31 and which transmits the pressure signal effect to the converter 11. This provides a mechanical amplification of the signal, i.e. a weak pressure pulse signal transmitted through the greater surface area A1 to a pressure transmission element, such as the pressure transmission element 31, is transmitted through the smaller surface area A2 to the converter 11 amplified by ratio A1/A2. In a preferred embodiment, each pressure transmission element, i.e. also the pressure transmission elements 32 to 38, is in its corresponding surface area A1, A2 similar to the pressure transmission element 31. Thus, in a preferred embodiment, the surface area A1 which is meant to be against the body 1 is in each pressure transmission element 31 to 38 greater than the surface area A2 against the converter 11. According to the findings of the applicant, a sufficient amplifying effect is achieved when, in a preferred embodiment, the surface area A1 of the area which is meant to be against the body 1, is at least 20% greater than the surface area A2 of the area against the converter 11 in the same pressure transmission element.

With reference to FIG. 1, to make the sensor structure 10 such that the sensitive surface which is to be against the body 1, i.e. the outer surface of the pressure transmission structure 30, 31 to 38, can be made to extend outward enough and, on the other hand, to keep the components processing the measurement signal in a protected location inside the measuring arrangement, then the structure of a preferred embodiment must be such that the extension H of the pressure transmission structure 30 comprising one or more pressure transmission elements 31 to 38 and located prior to the converter 11, between the area to be against the body 1 and the area against the converter 11 is at least triple in relation to the thickness J of the converter. It is noted that the thickness of the converter 11 refers to the distance of the inner surface of the ground plane 20 (the lower surface of the ground plane in FIG. 1) from the surface of the signal output, for instance the signal output 21. The circuit board 18 used as a platform for the signal outputs 21 to 28 is not calculated into the thickness of the converter 11.

In relation to the extension, it is noted that in a preferred embodiment, the extension H of the pressure transmission structure 30 comprising one or more pressure transmission elements 31 to 38 and located prior to the converter 11, is at least 1 mm in the direction between the surface to be against the body 1, i.e. the outer surface, and the converter 11. The extension H is, in a way, the height H of the pressure transmission structure, as seen in FIG. 1.

In a preferred embodiment, the measuring arrangement has multiple channels and consequently, the pressure transmission structure comprises two or more pressure transmission elements 31 to 38 for transmitting the effect of a pressure signal measurable from the body to the converter. In FIG. 2, there are two pressure transmission elements, i.e. elements 31 and 32, but the version in FIGS. 3 to 6 is more practical having even more pressure transmission elements, for instance 8, i.e. elements 31 to 38. FIGS. 1 to 2 and 5 to 6 show that the converter 11 comprises channel-specific conductive signal outputs 21 to 28, each signal output 21 to 28 forming a pair with the corresponding pressure transmission element 31 to 38. In FIGS. 1 to 2, the signal outputs 21 to 22 are the second electrodes of the converter, through which electrodes the electrical measuring signals are transmitted and from which electrodes the measuring signals are obtained for further processing. FIG. 8 concerns the signal outputs 212 to 128 which are resistive elements paired with pressure transmission elements 31 to 38. Thus, in practice, the effect of the movement of the pressure transmission element 31, for instance, on the converter can be detected by the electrical signal received from the signal element 21. The electrical signal is measured in relation to the ground plane 20. The resistive elements 121 to 128 acting as signal outputs 121 to 128 in FIG. 8 alter the magnitude of the electrical current running through each resistive element 121 to 128.

As shown in FIGS. 3 to 6, the multi-channel sensor structure is set crosswise to the artery 2 so as to make sure that the pressure pulse of the artery is detected. It is noted that the pressure transmission elements 31 to 38 are most preferably adjacent to each other to achieve a small size and a good measuring reliability. As shown in FIG. 4, the structure should most preferably be such that the surface formed by the adjacent pressure transmission elements 31 to 38, which is meant to be against the body 1, is curved, because this way the top of the pressure transmission structure in a way sinks into the skin 1, achieving good compression. It can be seen that the pressure transmission elements 31 to 38 are most preferably parallel, making the movements of the pressure transmission elements 31 to 38 towards the converter 11 and the return movement unidirectional, which does not require much space.

With reference to FIGS. 1 to 2, a most preferable structure is such that the surface meant to be against the body 1 in one or more pressure transmission elements 31 to 38 is such that the surface of the pressure transmission element, for instance the element 31, is further out in the mid-area C of the pressure transmission element 31 than at the sides E1, E2, thus making the surface of the pressure transmission element 31 curved. This embodiment, too, improves the ability of the pressure transmission element to push against the body. Most preferably, one or more pressure transmission elements 31 to 38 in the pressure transmission structure 30 are disciform, because with the form it is easy and quite simple to achieve the above-mentioned preferred embodiments.

Figure 11:
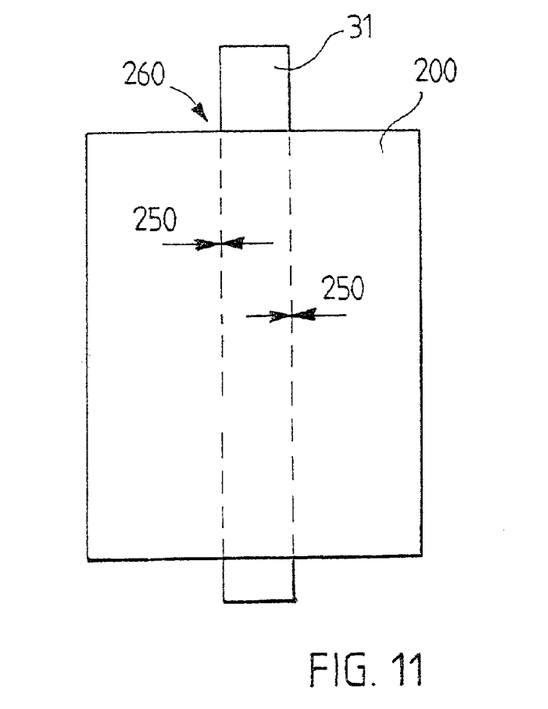
FIG. 11 illustrates the clearances between the pressure transmission element and the support structure.

With reference to FIGS. 1 to 2 and 11, in a preferred embodiment, the measuring arrangement comprises a support structure 200 against which one or more pressure transmission elements 31 to 38 of the pressure transmission structure are supported. The movement of the pressure transmission elements 31 to 38 can easily be enabled by means of the support structure. Between the support structure 200 and one or more pressure transmission elements 31 to 38, the measuring arrangement comprises a support enabling the movement of one or more pressure transmission elements of the pressure transmission structure towards the converter when the pressure transmission element has detected a pressure signal. In a preferred embodiment, the multi-channel measuring arrangement comprises a support structure 200 against which two or more pressure transmission elements of the pressure transmission structure 30 are supported. Between the support structure 200 and the pressure transmission elements, the measuring arrangement comprises supports enabling movement, which, after a pressure signal has been detected, enables both the movement of one or more pressure transmission elements towards the converter and the movement of the pressure transmission elements 31 to 38 between each other in the direction between the body 1 and the converter 2.

With reference to FIGS. 2 and 11, it is noted that to implement the support enabling the movement of the pressure transmission element, such as the element 31, the measuring arrangement comprises one or more clearances 250 between the support structure 200 and one or more pressure transmission elements. The clearance is most preferably at least 0.01 mm to enable a sufficient movement. The support structure 200 comprises a socket 260 for one or more pressure transmission elements of the pressure transmission structure. The clearance 250 is in the support structure between the pressure transmission element 31 and the socket 260 of the support structure 200. The socket 260 refers to the space in the support structure 200, where the pressure transmission element is. There is an opening both on the body 1 side and the converter 11 side in the socket 260 so as to allow the pressure signal of the artery 2 to move the pressure transmission element 31 towards the converter 11 and to allow a return movement.

Figure 10:
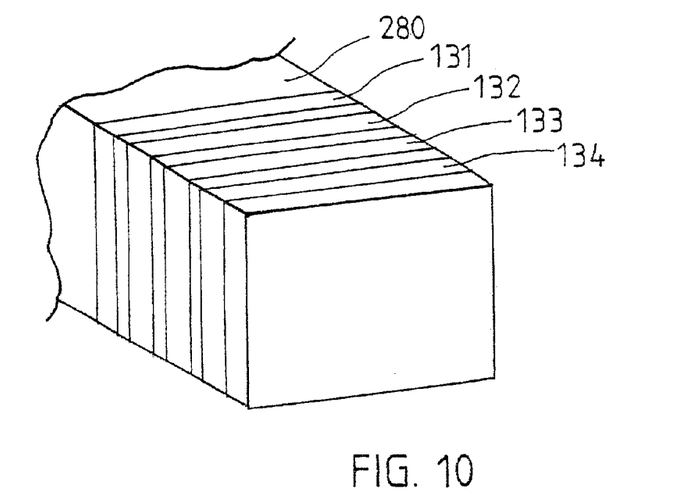
FIG. 10 shows a pressure transmission structure made of zebra rubber.

Alternatively, a solution presented in FIG. 10 is possible, in which to implement the support enabling the movement of one or more pressure transmission elements, the support structure 280 of one or more pressure transmission elements—having now reference numbers 131 to 134—of the measuring arrangement is made of a flexible material, and one or more pressure transmission element 131 to 134 of the pressure transmission structure are supported against this flexible support structure 280. In a preferred embodiment according to FIG. 10, the support structure 280 and one or more pressure transmission element 131 to 134 in it are made of zebra rubber which allows each pressure transmission element 131 to 134 to move at least somewhat in relation to the support structure 280. Zebra rubber is so called because of the stripes made up of dark and light areas, the light areas being the support structure 280 and the dark areas the pressure transmission elements 131 to 134.

In a preferred embodiment, one or more pressure transmission elements 31 to 38 and 131 to 134 are made of an insulating material preventing the skin from getting into contact with electrical signals.

As stated earlier, the measuring arrangement of the invention is one meant for measuring a pressure pulse of an artery 2 from the human body 1.

As for the fields of application of the invention, the primary field of application is that of the earlier patents and patent application of the applicant, i.e. personal, small-sized heart rate monitors for wrist use. The measuring arrangement in FIG. 5 is one meant for use in a heart rate monitor attached to a person's wrist or elsewhere. The wristband shown in FIG. 4 is marked with reference number 350.

In the application in question, the pressure transmission structure 30, 31 to 38 and the converter 11, 111 measure a pressure pulse of an artery 2 in the body 1 and, on the basis of this, the heart rate value can be calculated. The measuring arrangement is then one meant for measuring a pressure pulse of an artery 2 from the human body 1. As shown in FIG. 5, the measuring arrangement also comprises a definition means 400 connected to the converter 11 for determining the heart rate value on the basis of the pressure pulse measurement of the artery 2. Prior to the heart rate value definition means 400, there can be signal processing means known per se or other signal processing means, such as a filter 401, an amplifier 402, and an A/D converter 403. For simplicity's sake, only the amplifier 402 has been shown in FIG. 2, and for the same reason, it is shown connected only to signal output 31. It should, however, be noted that the amplifiers and filters perform action on signals of all channels.

The filter 401 in FIG. 5 is a band-pass filter. The pass band of a band-pass filter is most preferably in the range of 1 to 10 Hz, for instance.

In FIG. 5, the filter 401 and the amplifier 402 perform an analogue pre-stage. In FIGS. 4 and 5, the measuring arrangement also comprises a display 410 connected to the definition means 400 for displaying the heart rate value. In an embodiment, the definition means 400 calculates the number of received pressure pulses for a time unit and indicates the heart rate value on the display 410. In another embodiment, the definition means 400 measures the time slots between consecutive pressure pulses and calculates the heart rate on the basis of the obtained information, the heart rate is then shown on the display 410. In addition, the definition means 400 is connected to a memory unit 411 and a transmission path 412, such as an RS-232 link, through which the heart rate information can be transmitted to a reader and on to a PC, for instance. Naturally, transmission path 412 can also be used for data transmission in the opposite direction.

FIG. 6 shows a preferred embodiment for blood pressure measurement. The measuring arrangement is then one meant for measuring a pressure pulse of an artery from the human body 1. The measuring arrangement also comprises a pulse strength definition means 500 connected to the converter 11 for determining the strength of the pressure pulse of an artery 2. In addition, the measuring arrangement comprises a sensor 601 measuring the magnitude of the active pressure generated by a pressure generator 600, which sensor has a wire or wireless connection 602 to the measuring arrangement and which can, in this application, be seen as part of the measuring arrangement. The active pressure refers to the pressure which presses the vein closed. By sufficient active pressure, the pressure pulse ceases, i.e. the pressure transmission means 31 to 38 do not detect a pressure pulse and no measuring signal proceeds to block 500. When the magnitude of the active pressure becomes smaller, i.e. when the pressure of the pressure generator is lowered, blood starts to flow again and the pressure transmission structure 31 to 38 generates a signal through the converter 11, 111 to block 500 which then determines the magnitude of the pressure pulse. The pressure generator 600 is, for instance, a pressure sleeve 600, and comprises a pressure pump 600*a* and a pressure conductor 600*b* by means of which the pressure is transmitted from the pressure pump 600*a* to the sleeve 600.

In the embodiment of FIG. 6, too, the measuring arrangement comprises a filter 701, an amplifier 702, an A/D converter 703, a display 710, a memory unit 711 and possibly a data transmission path 712, such as an RS link 712. As for their implementation, reference is made to the corresponding blocks in FIG. 5.

The value of the active pressure generated by the pressure generator 600, or information from which the value of the active pressure can be calculated is transmitted from the sensor 601 to the measuring arrangement through the RS-323 link 712 or through another wire or wireless data transmission connection. The transmission link in question is marked with reference number 602. The transmission link 602 can, for instance, be based on an inductive connection between blocks 601 and 712, which is based on resonance circuits implemented by means of coils and capacitances which, however, need not be described in greater detail herein.

Figure 7:
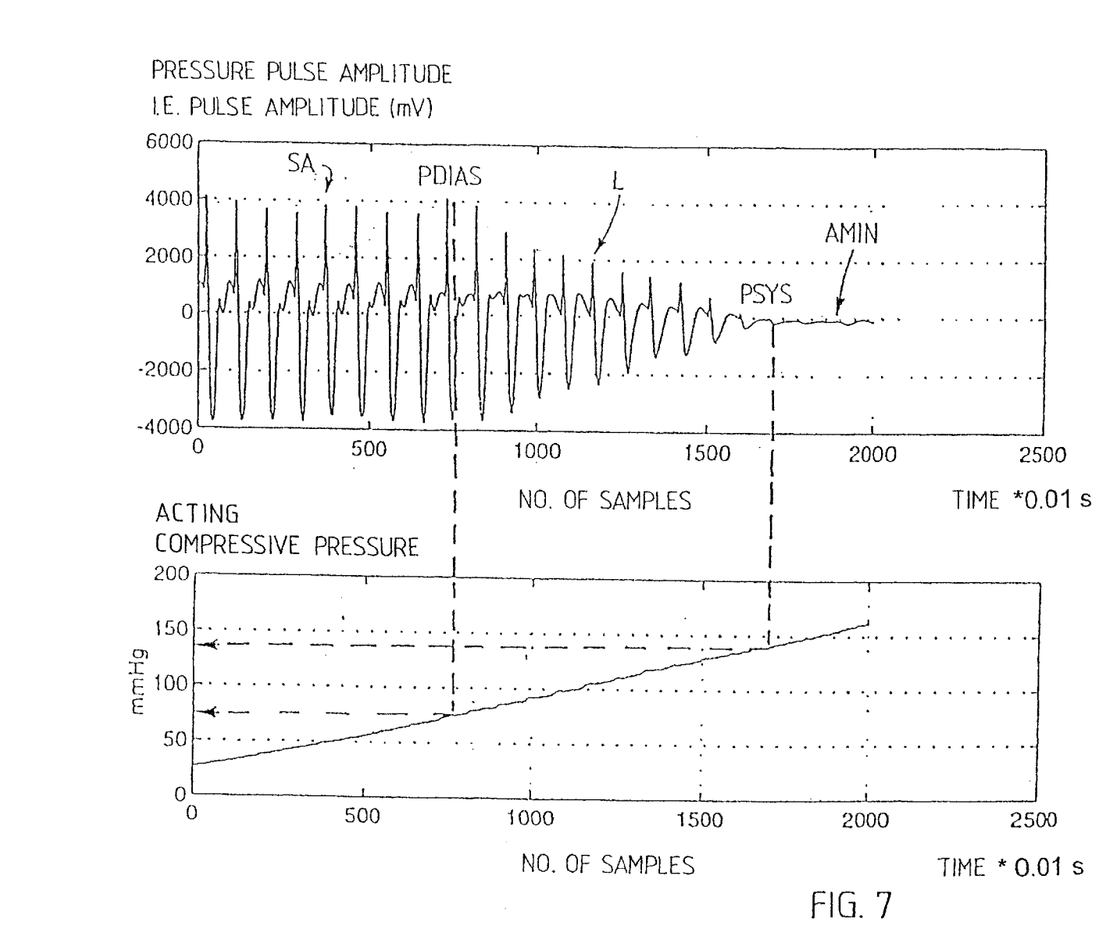
FIG. 7 shows a pressure pulse signal in blood pressure measurement and an active compressive pressure.

The measuring arrangement in FIG. 6 also comprises a blood pressure definition means 800 connected to the pressure pulse strength definition means 500. The blood pressure definition means 800 also receives information on the magnitude of the active pressure through the link 712, 602 from the sensor 601. Controlled by the pressure pulse strength definition means 500, the blood pressure definition means 800 determines, on the basis of the signal from the sensor 601 measuring the magnitude of the active pressure, the blood pressure value which is then displayed on the display 710 of the measuring arrangement. With reference to FIGS. 6 to 7, it is noted that when the signal of the pressure pulse strength definition means 500 begins to decrease, the blood pressure definition means 800 determines, i.e. finds out, that the diastolic pressure value PDIAS is that of the currently active pressure received from the sensor 601. Correspondingly, when the signal amplitude of the pressure pulse strength definition means 500 becomes low enough, or is no longer detected, or approaches a limit value close to zero, the blood pressure definition means 800 determines, i.e. finds out, that the systolic pressure value PSYS is that of the currently active pressure received from the sensor 601.

With reference to FIGS. 6 to 7, it is noted that said variable active pressure is a rising active pressure. In this case, the blood pressure measurement is performed when the active pressure is raised with the pressure generator 600. Measurement during rising pressure is more comfortable for the person whose blood pressure is being measured, because the active pressure need not be raised too high. The situation then is that in a measurement made during rising active pressure, the diastolic pressure PDIAS is determined on the basis of the active pressure which prevails when, during pressure pulse measurement, such as the measurement of its amplitude, it is detected in blocks 500 and 800 that the magnitude of the pressure pulse, i.e. its amplitude, for instance, begins to decrease. Correspondingly, the determination of the systolic pressure PSYS is performed on the basis of the active pressure which prevails when, during pressure pulse measurement, such as the measurement of its amplitude, it is detected in blocks 500 and 800 that the decrease in the amplitude of the pressure pulse ends.

To be more precise, and still referring to FIG. 7, the method is most preferably such that in a measurement performed during a rising active pressure, the determination of the diastolic pressure PDIAS is performed on the basis of the active pressure which prevails when, during pressure pulse measurement, such as the measurement of its amplitude, it is detected that the substantially standard value of the pressure pulse, such as the standard amplitude, begins substantially directly to decrease linearly. In FIG. 7, the standard amplitude area is marked with SA and the linear area is marked with L. Correspondingly, the determination of the systolic pressure PSYS is performed on the basis of the active pressure which prevails when, during pressure pulse amplitude measurement, it is detected that the decrease of the substantially direct linearly decreasing pressure pulse amplitude ends and reaches its minimum value AMIN which substantially corresponds to zero. The detection of such points is easier by means of the pulse strength definition means 500, and, in addition, a more accurate measurement is obtained.

The heart rate definition means 400, the pulse strength definition means 500 and the blood pressure definition means 800 can be implemented by a programmable processor, an application-specific integrated circuit, separate components or by what is known as composite technology. Composite technology refers to a combination of two or more technologies mentioned above. The above implementation alternatives also apply to the filter 401 and the amplifier 402, for which, in the applicant's opinion, the ASIC implementation is especially good, but the use of operational amplifiers, resistors and capacitors is also a possibility. The display 410 can be a matrix display, for instance.

In FIG. 6, the implementation of blocks 701 to 702 and 710 to 712 can be quite similar to that of blocks 401 to 402 and 410 to 412 in FIG. 5. The most significant difference is in blocks 500 and 800 as compared with block 400, since block 500 must, in comparison with block 400, be able to find out the magnitude of the pressure pulse signal at each time instant instead or in addition to calculating solely the number of pulses (or the lengths of the time slots between the pulses). Also, block 800 must be able to interpret what the change in the output information from block 500 means. The operation of block 800 is thus controlled by rules which indicate according to FIG. 7 what each change in the output information from block 500 means. FIGS. 5 to 6 show that the converter 11 is connected to the filter 401/701 in which the signal is filtered. The filter 401/701 is also connected to the amplifier 402/702 which amplifies the filtered signal. The amplifier 402/702 is also connected to the A/D converter 403/703 which converts the signal from analogue to digital. The A/D converter is also connected to the processor 400/500/800. As was done with FIGS. 4 and 5, it can also be noted with reference to FIGS. 4 and 6 that in a preferred embodiment, the measuring arrangement is one meant to be used in a blood pressure gauge attached to a person's wrist or elsewhere. The wristband shown in FIG. 4 is marked with reference number 350.

It is further noted with reference to FIG. 4 that the platform 18, for instance a circuit board, can be two-sided so that the signal outputs 21 to 28 are on one side and blocks 400 to 403 and 410 to 412 are on the other side of the platform 18. The same applies to blocks 701 to 703 and 710 to 712 and 800 of the blood pressure gauge. In FIG. 4, the blocks 400 to 403 and 411 to 412 of FIG. 5 or, on the other hand, the blocks 701 to 703 and 711 to 712 and 800 of FIG. 6 are simply marked with EL. The casing of the heart rate monitor or blood pressure gauge is marked with reference number 900.

It is obvious to a person skilled in the art that as technology advances, the basic idea of the invention can be implemented in many different ways. The invention and its embodiments are thus not limited to the above examples but can vary within the scope of the claims.

What is claimed is:

1. A measuring arrangement for measuring a pressure signal from a living body including a sensor structure which comprises a converter for converting the effect of the pressure signal measured from the body to an electrical signal comprising:

a pressure transmission structure, said pressure transmission structure being a mechanical connection piece positionable between said converter and the body, said pressure transmission structure further comprises one or more pressure transmission elements and which pressure transmission structure is adapted through said one or more pressure transmission elements, for direct or indirect contact with the body for detecting the pressure signal measurable from the body, and which pressure transmission structure is, through said one or more pressure transmission elements, mechanically connected to the converter for transmitting the effect of the pressure signal detected in the body by said one or more pressure transmission elements to the converter of the sensor structure, and wherein said pressure transmission elements have a disc form structure.

2. A measuring arrangement as claimed in claim 1, wherein said one or more pressure transmission elements have a first surface area, and a second surface area, said first surface area being positionable against the body to detect the pressure signal of the body, said first surface area being greater than said second surface area, said second surface area being positionable against the converter in the same pressure transmission element and which is meant to transmit the pressure signal effect to the converter.

3. A measuring arrangement as claimed in claim 2, wherein in a pressure transmission element, the surface area which is to be against the body is at least 20% greater than the surface area which is against the converter in the same pressure transmission element.

4. A measuring arrangement as claimed in claim 1, wherein an extension of the pressure transmission structure comprising one or more pressure transmission elements and located prior to the converter, between the area to be against the body and the area against the converter is at least triple in relation to the thickness of the converter.

5. A measuring arrangement as claimed in claim 1, wherein extension of the pressure transmission structure comprising said one more pressure transmission elements and located prior to the converter, is at least 1 mm in the direction between the surface to be against the body and the converter.

6. A measuring arrangement as claimed in claim 1, wherein the measuring arrangement has multiple channels and, thus, the pressure transmission structure comprises two or more pressure transmission elements for transmitting the effect of a pressure signal measured from the body to the converter.

7. A measuring arrangement as claimed in claim 6, wherein the pressure transmission elements are adjacent to each other.

8. A measuring arrangement as claimed in claim 7, wherein said pressure transmission elements form a surface for placing against the body and said surface is curved.

9. A measuring arrangement as claimed in claim 6, wherein the pressure transmission elements are parallel to each other.

10. A measuring arrangement as claimed in claim 6, wherein the multi-channel measuring arrangement comprises a support structure against which two or more pressure transmission elements of the pressure transmission structure are supported and that between the support structure and the pressure transmission elements, the measuring arrangement comprises supports enabling movement, which, after a pressure signal has been detected, enables both the movement of said two or more pressure transmission elements towards the converter and the movement of the pressure transmission elements between each other.

11. A measuring arrangement as claimed in claim 1, wherein said pressure transmission elements form a surface for placing against the body and one or more pressure transmission elements is such that the surface of the pressure transmission element is further out in the mid-area of the pressure transmission element than at the sides, thus making the surface of the pressure transmission element curved.

12. A measuring arrangement as claimed in claim 1, wherein the measuring arrangement comprises a support structure against which one or more pressure transmission elements are supported.

13. A measuring arrangement as claimed in claim 12, wherein between the support structure and said one or more pressure transmission elements, the measuring arrangement comprises a support enabling the movement of said one or more pressure transmission elements of the pressure transmission structure towards the converters when the pressure transmission element has detected a pressure signal.

14. A measuring arrangement as claimed in claim 13, wherein to implement the support enabling the movement of said one or more pressure transmission elements, the measuring arrangement comprises one or more clearances between the support structure and said one or more pressure transmission elements.

15. A measuring arrangement as claimed in claim 14, wherein the support structure comprises a socket for said one or more pressure transmission elements of the pressure transmission structure and that clearance is in the support structure between the pressure transmission element and the socket of the support structure.

16. A measuring arrangement as claimed in claim 13, wherein to implement the support enabling the movement of said one or more pressure transmission elements, the support structure said of one or more pressure transmission elements of the measuring arrangement is made of a flexible material, and that said one or more pressure transmission elements of the pressure transmission structure are supported against this flexible support structure.

17. A measuring arrangement as claimed in claim 1, wherein said one or more pressure transmission elements are made of an insulating material.

18. A measuring arrangement as claimed in claim 1, wherein the converter of the sensor structure, to which the pressure transmission structure is connected, is a capacitive converter whose capacitance changes according to the pressure transmitted by the pressure transmission structure to the converter.

19. A measuring arrangement as claimed in claim 18, wherein the capacitive converter comprises a conductive ground plane, one or more conductive signal outputs and an intermediate part between the ground plane and each signal output.

20. A measuring arrangement as claimed in claim 19, wherein the pressure transmission structure is connected to the converter through the ground plane of the converter.

21. A measuring arrangement as claimed in claim 1, wherein the converter of the sensor structure, to which the pressure transmission structure is connected, is a resistive converter whose resistance changes according to the pressure transmitted by the pressure transmission structure to the converter.

22. A measuring arrangement as claimed in claim 1, wherein the converter comprises one or more channel-specific signal outputs, each signal output being paired with the corresponding pressure transmission element.

23. A measuring arrangement as claimed in claims 21, wherein in the resistive converter, the signal outputs are resistive elements.

24. A measuring arrangement as claimed in claim 1, wherein the measuring arrangement is one meant for measuring a pressure pulse of an artery in a human body.

25. A measuring arrangement as claimed in claim 1, wherein the measuring arrangement is one meant for measuring a pressure pulse of an artery, and that the measuring arrangement also comprises a definition means connected to the converter for determining the heart rate on the basis of measuring the pressure pulse of the artery, and that the measuring arrangement also comprises a display connected to the definition means for displaying the heart rate value.

26. A measuring arrangement as claimed in claim 1, wherein the measuring arrangement is for use in a heart rate monitor attached to a person's hand, or wrist.

27. A measuring arrangement as claimed in claim 1, wherein the measuring arrangement is one meant for measuring a pressure pulse of an artery in a human body, and that the measuring arrangement also comprises a pulse strength definition means connected to the converter for determining the strength of the pressure pulse of the artery, and that a sensor is connected to the measuring arrangement, measuring the strength of the active pressure generated by a pressure generator, and that the measuring arrangement comprises a blood pressure definition means which from the signal of the pressure pulse strength definition means determines the blood pressure value on the basis of the signal from the sensor measuring the magnitude of the active pressure, the blood pressure value then being shown on the display of the measuring arrangement.

28. A measuring arrangement as claimed in claim 1, wherein the measuring arrangement is for use in a blood pressure gauge attachable to a person's hand, or wrist.

\* \* \* \* \*

UNITED STATES PATENT AND TRADEMARK OFFICE
CERTIFICATE OF CORRECTION

PATENT NO. : 6,616,612 B1
DATED : September 9, 2003
INVENTOR(S) : Nissila et al.

It is certified that error appears in the above-identified patent and that said Letters Patent is hereby corrected as shown below:

<u>Title page,</u>
Item [12], reads "Nissiläet al." should read -- Nissilä et al. --

<u>Column 12,</u>
Line 39, reads "an artery, and" should read -- an artery in a human body, and --

Signed and Sealed this

Twenty-fourth Day of February, 2004

JON W. DUDAS
*Acting Director of the United States Patent and Trademark Office*